(12) United States Patent
Brandeis (10) Patent No.: US 8,545,433 B2
(45) Date of Patent: Oct. 1, 2013

(54) APPARATUS AND METHOD FOR TREATING SPIDER VEINS

(75) Inventor: Zeev Brandeis, Rosh Haayin (IL)

(73) Assignee: V.V.T. Med Ltd., Kfar-Saba (IL)

( * ) Notice: Subject to any disclaimer, the term of this patent is extended or adjusted under 35 U.S.C. 154(b) by 188 days.

(21) Appl. No.: 12/416,966

(22) Filed: Apr. 2, 2009

(65) Prior Publication Data

US 2010/0106081 A1 Apr. 29, 2010

Related U.S. Application Data

(60) Provisional application No. 61/041,947, filed on Apr. 3, 2008.

(51) Int. Cl.
*A61M 1/00* (2006.01)

(52) U.S. Cl.
USPC ............... 604/30; 604/27; 604/191; 604/208

(58) Field of Classification Search
USPC ............... 604/27, 28, 173, 191, 208–210, 30, 604/36, 43
See application file for complete search history.

(56) References Cited

U.S. PATENT DOCUMENTS

| | | | | |
|---|---|---|---|---|
| 2,502,639 | A * | 4/1950 | Blake | 604/210 |
| 6,962,576 | B2 * | 11/2005 | Sibbitt | 604/191 |
| 2003/0120217 | A1 * | 6/2003 | Abergel | 604/191 |

* cited by examiner

*Primary Examiner* — Emily Schmidt (57) ABSTRACT

There is provided herein a system, device and methods for performing minimally invasive spider vein treatments. In some embodiments an apparatus for eliminating spider veins comprises a dual syringe mechanism that includes a pusher for pushing sclerosant materials into a target vein, and an extractor for extracting debris from a target vein; a needle for application into a target vein; and a Y-connector connecting each exit of the dual syringe mechanism to the needle. In some implementations the apparatus's dual syringe mechanism includes a locking mechanism to enable controlled advancing of the syringe pusher.

8 Claims, 6 Drawing Sheets

APPARATUS AND METHOD FOR TREATING SPIDER VEINS

CROSS REFERENCE TO RELATED APPLICATIONS

This application claims priority from U.S. Provisional Patent Application No. 61/041,947, filed 3 Apr. 2008, entitled "APPARATUS AND METHOD FOR TREATING SPIDER VEINS", which is incorporated in its entirety herein by reference.

FIELD OF THE INVENTION

The present invention relates to methods and devices useful in treating veins. Specifically, embodiments of the present invention relate to systems, methods and apparatuses that provide methods and apparatus for treating small veins, such as spider veins.

BACKGROUND OF THE INVENTION

Spider veins, also known as Telangiectasias, are small dilated blood vessels near the surface of the skin or mucous membranes, typically measuring between 0.5-1 mm in diameter. They can develop anywhere on the body but are commonly seen on the face around the nose, cheeks, and chin. They can also develop on the legs, specifically on the upper thigh, below the knee joint, and around the ankles.

Current treatments for eliminating telangiectasiae include sclerotherapy, considered the "gold standard", whereby sclerosant medication is injected into the diseased vein so it hardens and eventually shrinks away, and laser, whereby a light beam is pulsed onto the veins in order to seal them off and cause them to dissolve. Sclerotherapy is generally preferred over laser for and smaller varicose leg veins, and varicose veins and reticular leg veins, if present, must be treated prior to any treatment of the telengiectasia.

Another treatment method, often attempted following unsuccessful sclerotherapy, is stab phlebectomy. This involves the use of a special local anesthetic that is injected into the area surrounding the vein. The doctor then removes the entire problem vein through a small incision.

Light-based treatments generally require adequate heating of the veins, with potential side effects of buring in adjacent areas. For optimal results, several laser treatments are usually necessary. Varicose veins can also be treated with foam sclerotherapy, endovenous laser treatment, radiofrequency ablation or open surgery.

It is noted, however, that sclerotherapy has certain negative side effects, such as an irregular coloring on the skin, and the appearance of reddish blood vessels appearing around the treated area, which would require further injections. It is important to select a pratitionist with adequate training in sclerotherapy and is well versed in the different types of sclerosing agents available.

It would be highly advantageous to have a system and method of treating spider veins and small varicose veins in a way that is minimally invasive, yet safe and highly effective, that does not require excessive usage of sclerosing agents or laser therapy.

SUMMARY OF THE INVENTION

There is provided, in accordance with an embodiment of the present invention, an apparatus, system, and method for performing minimally invasive spider vein treatments. In some embodiments an apparatus for eliminating spider veins comprises a dual syringe mechanism that includes a pusher for pushing sclerosant materials into a target vein, and an extractor for extracting debris from a target vein; a needle for application into a target vein; and a Y-connector connecting each exit of the dual syringe mechanism to the needle. In some implementations the apparatus's dual syringe mechanism includes a locking mechanism to enable controlled advancing of a syringe pusher. In some examples the locking mechanism may enable controlled aspirating from the target vein into a syringe pusher.

According to some embodiments, a method is described for deploying sclerosing materials into spider veins, comprising: entering a small gauge needle into a target vein, where the needle is connected to a dual syringe apparatus; extracting liquid compounds from the target vein, using one of the dual syringe's pushers; and deploying low concentration sclerosant material into the target vein, using a second of the dual syringe's pushers. In some implementations the method may further comprise deploying of sclerosant material only after blood is extracted from the target vein. In other embodiments the sclerosant material may deployed substantially simultaneously to the extracting of blood from the target vein. In further methods a lockable apparatus may be used to control the extracting of the liquid compound, and the deploying of the sclerosant material.

According to some embodiments, a vein treatment device is provided for ablating small veins, comprising: a small gauge needle for application into a target vein; a dual syringe mechanism having a first exit for pushing sclerosant materials into a target vein, and having a second exit for extracting debris from a target vein; and a Y-connector connecting each exit of the dual syringe mechanism to the needle. In further embodiments the pushing of sclerosant materials and extracting of debris is substantially simultaneous. In other embodiments the treatment device may include a syringe locking mechanism, which may be adapted to provide stage by stage controlling of the pushing of sclerosant materials and the extracting of debris. In some implementation examples the stage by stage controlling is setup to provide increments of volumes ranging between 0.05 milliliters to 5 milliliters.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

It will be appreciated that for simplicity and clarity of illustration, elements shown in the drawings have not necessarily been drawn to scale. For example, the dimensions of some of the elements may be exaggerated relative to other elements for clarity. Further, where considered appropriate, reference numerals may be repeated among the drawings to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

Spider veins or Telangiectasias are the smallest blood vessels evacuating blood from the different tissues. Spider veins have small diameters (e.g., less than 1 mm inner diameter), are very peripheral, and in many cases they can be seen externally. Spider veins are very sensitive to exposure to chemicals, sun rays, physical impacts, weather and environmental conditions. A range of physical conditions and diseases may cause spider veins to become bulky, congested, dilated and bold, which result in dense mesh of veins, with or without discoloration of the skin. Present treatments for dilated spider veins, or Telangiectasias, include freezing using CO; direct injections with salt solution (e.g., 20% salt solution), different kinds of sclerosing agents, low intensity superficial laser treatments, Intensive Pulsed Light (IPL) therapy, and low intensity superficial ultra sound/radio frequency radiation treatments. The above mentioned treatments are geared towards causing blood clots inside a section of the spider vein, which results in ceasing the blood flow and eliminating the vein. The above treatments, moreover, are sensitive to discoloration of the skin, especially when using laser or ultrasound treatments (treatments may cause changes in the skin pigmentation).

The term "spider veins" as used herein may refer to small varicose veins, surface veins, and other small veins. The term "sclerosant" as used herein may refer to any suitable liquid substance, or even foam based substance, that may be used to treat veins, including salt solution, medicinal compounds, or other suitable treatment materials. The term "debris" as used herein may refer to a variety of unwanted elements in a treatment area, such as blood, sclerosant material, scar tissue etc.

Embodiments of the present invention enable controlled sclerosing or ablation of spider veins in a substantially non-invasive way. In some embodiments rapid, effective and safe spider vein treatments may be enabled using a combined sclerosing-aspiration procedure. Further, the combined sclerosing-aspiration procedure may enable effective treatments using minimal sclerosant materials, thereby minimizing the risk of skin de-colorization.

Since spider veins are very superficial, their treatment often impacts on the skin pigmentation, causing skin de-colorization. As such these veins demand sensitive treatment that avoids or minimizes. Treatment that includes evacuating congested debris, such as blood, in addition to injecting highly diluted low concentration sclerosant (e.g., SDS, salt solution or Polydoconol) may enable effective vein elimination using lower concentration sclerosant, thereby resulting in minimal pigmentation damage. Furthermore, in some embodiments, treatment using blood aspiration and sclerosant deployment may enable very precise penetration into the target capillary or vein, by allowing the treatment provider to confirm that the needle is in the target vein before carrying out the treatment. Such an application may prevent the injection of the sclerosant into tissue that is not the capillary being treated.

Figure 1:
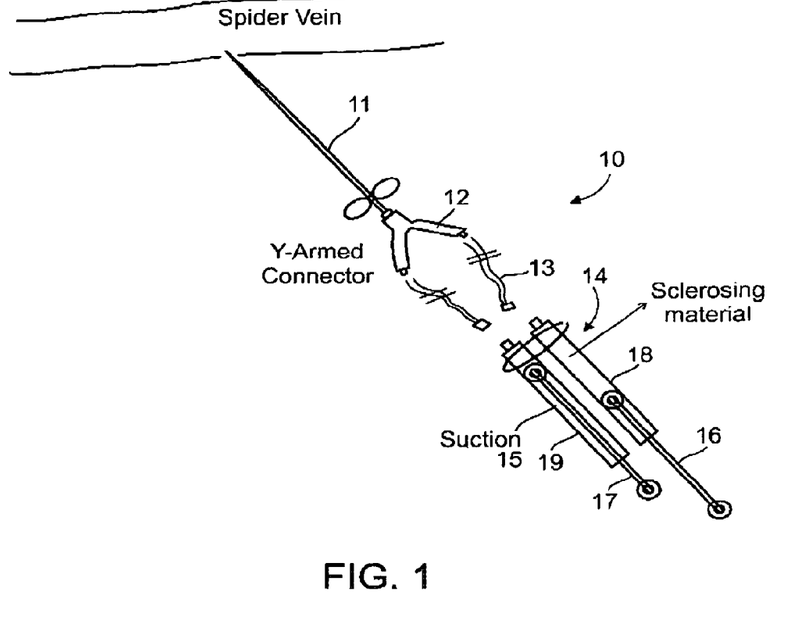
FIG. 1 is a schematic diagram illustrating an apparatus for enabling spider vein treatment, according to some embodiments.

Reference is now made to FIG. 1 which is a schematic block diagram illustrating an apparatus 10 for enabling spider vein treatment, according to some embodiments. As can be seen in FIG. 1, apparatus 10 may include a small gauge needle 11, for example a butterfly needle, with a control mechanism, for example, a Y-armed needle 12. The control mechanism may include a dual or multiple control mechanism, for controlling two or more catheter channels, tubes or lumen. Needle 11 may have a bore or hole that is small enough to enter the target vein(s). Apparatus 10 may include at least a dual connection pipe 13, to connect the Y-arms to the syringe plunger 14. Connection pipe 13 may be constructed from silicon, plastic or other suitable materials, to help provide maneuverability to the plunger apparatus (14).

Plunger apparatus 14 may be at least a dual plunger, adapted to enable independent operation of at least 2 syringe canals, barrels or reservoirs 18 and 19. Dual plunger apparatus 14 may include the individual plunger or reservoirs 18 and 19 that are coupled or joined together, so as to be held and operated as a single unit or apparatus. Reservoirs 18 and 19 may be empty or may include treatment materials or agents, for example, sclerosing agents, medications, drugs etc. Plunger apparatus 14 may be controlled using at least 2 plunger controllers 16 and 17, to enable independent, dependent or simultaneous operation of reservoirs 18 and 19. For example, controller 17 may be used to inject a liquid medical substance, such as sclerosing agents, into a target vein, the sclerosing agents being stored prior to treatment in reservoir 19. Additionally, controller 16 may be used to aspirate, withdraw, suck or otherwise remove elements, such as blood, debris etc., from a target vein, either before, during or after sclerosing treatment, entering aspirated materials into reservoir 18.

According to some embodiments, plunger apparatus 14 may include a double plunger controller device, to enable same motion controlling of reservoirs 18 and 19. For example, control mechanism 16 may be constructed so as to require a pushing action to extract contents from a vein, and a pulling action to insert agents into the vein. Such a simplified procedure may enable an operator of the device to substantially implement the sclerosing-aspiration procedure with a single hand. In this way, same direction actions by both controllers 16 and 17 may enable simplified maneuverability of treatment apparatus 10. For example, such a procedure may be implemented using a push-pull technology needle such as that used in patent application No. 60/626,874, titled "Device and Method for Treating a Vessel", by a common inventor, which is hereby incorporated fully herein. Further embodiments can be used with a 2-part needle, which includes two separate lumen in the needle that may be independently controlled. Another example may use a dual-control Nitinol needle, or other suitable controllable needles using memory materials etc. According to some embodiments a dual control syringe may be used, whereby one controller or pusher mechanism may be used to implement the dual push-pull action, enabling easy use by the device operator. In the above cases the dual syringe may be used to enable simultaneous withdrawing and entering of blood/sclerosant, thereby enabling the operator of the device to maintain substantially constant pressure in the target vessel. Such an approach enables the operator to control the pressure in the target vessel, and to carry out the procedure with substantially minimal dilution of sclerosant materials. An advantage of such an approach is that a relatively minimal dosage of sclerosant material may be required to affect the vessel elimination, therefore minimizing the risk of pigment damage and other risks and damages resulting from excessive exposure to sclerosing materials.

According to some embodiments of the present invention, the two plungers or syringe controls may be operated independently. For example, a first plunger may be used to extract blood from a target vein, and a second plunger may be used to enter sclerosant material into the target vein.

Figure 2A:
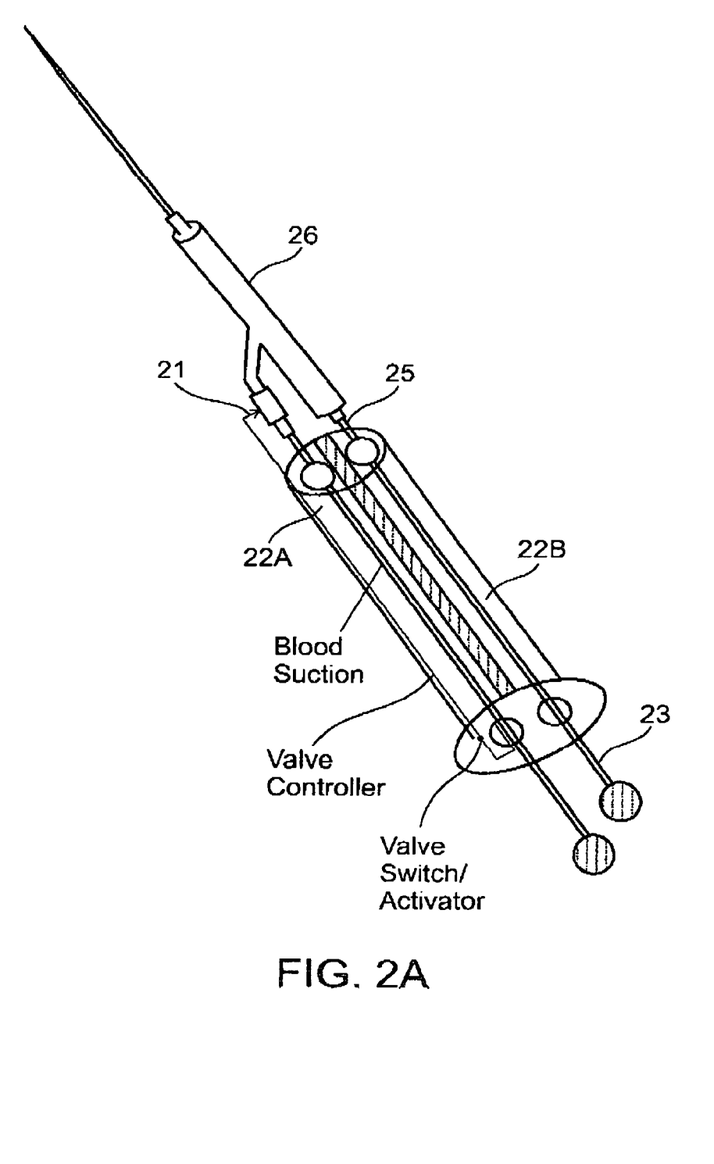
FIGS. 2A and 2B are schematic block diagrams of dual syringe loading mechanisms, according to some embodiments.

Reference is now made to FIG. 2A, which is a schematic drawing showing a syringe loading mechanism for both entering sclerosing agents into a target vein and extracting or aspirating blood or other elements from the target vein, according to some embodiments. As can be seen in FIG. 2A, the syringe loader may have 2 independent channels or reservoirs 22A and 22B, that may be controlled (e.g., pulled or pushed) independently. In such a case, the syringe reservoir 22A that substantially handles the aspiration of the blood may include or be coupled to a valve or channel lock 21 that may be engaged or disengaged, to lock the blood aspirating syringe reservoir 22A when the sclerosant injecting syringe 23 is injecting sclerosant materials, to ensure that the sclerosant materials enter the target vein and not the blood extraction syringe or its reservoir. The valve element may be coupled to the reservoir, the syringe inlet/outlet pipe 25, or the Y-connector 26. Typically the valve or channel lock is engaged by an operator using a mechanical switch connected to the syringe pusher, which opens the valve to receive blood or other materials only when the pusher is being pulled. This may enable the quantity of sclerosant materials and/or blood to be deployed and/or aspirated to be controlled.

Figure 2B:
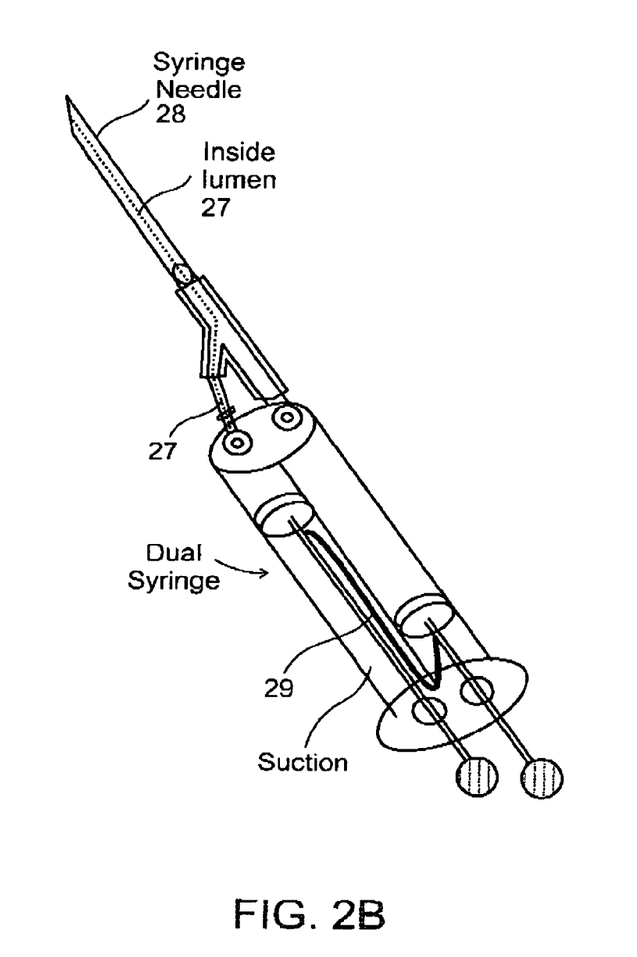

Reference is now made to FIG. 2B, which is a schematic drawing showing a syringe loading mechanism for both entering sclerosing agents into a target vein and extracting or aspirating blood or other elements from the target vein, according to some embodiments. As can be seen in FIG. 2B, the syringe loader may have 2 co-dependent channels or reservoirs that may be operated in parallel, wherein the one channel is coupled to a lumen 27 (indicated by the dotted line) that runs internally of a syringe needle 28 (hereinafter referred to as inside lumen). For example, as the one syringe pusher that controls the sclerosing materials is pushed, the sclerosant materials will be deployed through the needle into the target vein. Since the two syringe pushers are connected by a limited length connector 29, the pushing of the first pusher will lead to a corresponding "pulling" or extraction of the second pusher, which will cause the extraction of blood or other materials from the target vein, through the inside lumen. Such a configuration may enable the quantity of sclerosant materials and/or blood to be deployed and/or aspirated to be controlled.

Figure 3A:
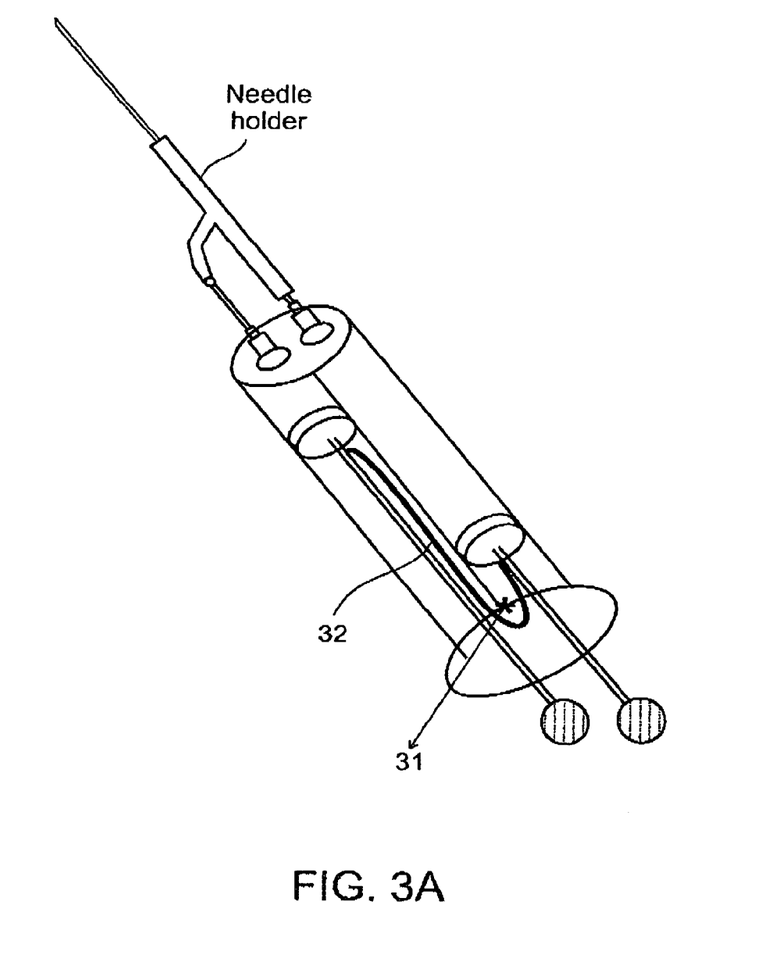
FIGS. 3A and 3B are a schematic diagrams illustrating a syringe locking mechanism that may used in implementing a spider vein treatment, according to some embodiments.

In a further embodiment, as can been in FIG. 3A, a syringe pusher with a locking mechanism or lockable apparatus 31, 32 may be used, for example, to lock the syringe pushers in a variety of positions, according to the desired volume of sclerosant to be injected into a target vein, or the volume of blood to be aspirated from a target vein. In one example a ratchet device 31 may be used to lock the pusher in place. In another embodiment a teeth-like catching apparatus may be configured on the pushing mechanism, for example, as used on common adjustable forceps-type devices, with one or more control or catch points, for example, at each ml mark, to enable locking of the pulling/pushing process at each ml of fluid content. In such configurations the syringe pusher may enable an operator of the vein treatment apparatus to carefully control the entry of elements such as sclerosant materials into a target vein and/or the extraction of blood or other elements from the target vein. This may be implemented by advancing the pushing/pulling of the syringe pusher(s) according to a measured degree, and optionally locking the positions of the syringe pusher(s) in a variety of positions, for example, to restrict further entering and/or extracting of materials to/from target veins. Embodiments of syringe pusher apparatus with locking mechanisms may be used in conjunction with syringe pushers with co-dependent reservoirs, and/or with syringe pushers with independent reservoirs. In some embodiments, a dual action syringe is used, for example, which may include a limited length connector 32 that connects the two syringe plungers. In this way the "pushing" of the first pusher will lead to a corresponding "pulling" or extraction of the second pusher, to enable pushing of one plunger that causes a simultaneous pulling of the second plunger. In such an embodiment the locking mechanism 31, 32 may be used to enable the quantity of sclerosant materials and/or blood to be deployed and/or aspirated to be controlled.

Figure 3B:
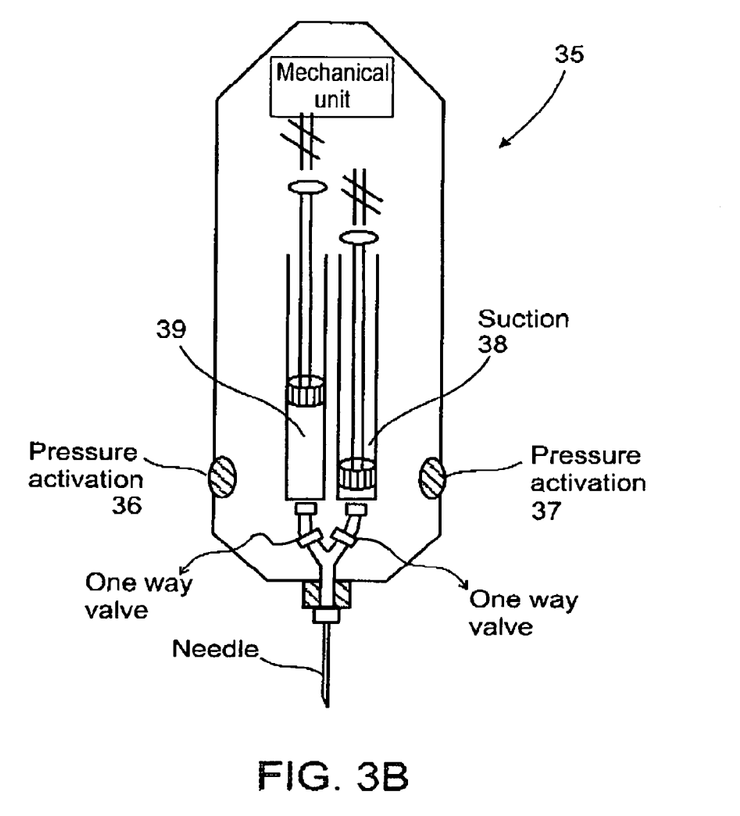

In a further embodiment, as can been in FIG. 3B, a syringe pusher with a locking mechanism or lockable apparatus 35 may be used. For example, a hand held automatic spider vein eliminator apparatus may be used to lock the syringe pusher in a variety of positions, according to the desired volume of sclerosant to be injected into a target vein, or the volume of blood to be aspirated from a target vein. As can be seen in the figure, a controllable dosage mechanism, for example, a ratchet type mechanism or other stage by stage lockable mechanism, controlled via one or more switches or buttons 36, may be used for safely advance the treatment pusher 39 of treatment materials into the target vein. Alternatively or additionally, a ratchet type mechanism or other stage by stage lockable mechanism, controlled via one or more switches or buttons 37, may be used to safely aspirate or remove treatment materials, debris, blood etc. from the treatment area, using the suction pusher 38.

In some embodiments the hand held automatic spider vein eliminator apparatus 35 may require finger pressure, optionally from one hand, from the operator to release and/or aspirate materials, to enable well controlled deployment and/or aspiration of sclerosants, medicinal materials, blood, debris, etc. According to some embodiments highly accurate predefined or user defined quantities of materials may be deployed and/or aspirated, for example, in increments of volumes ranging between 0.05 milliliters to 5 milliliters.

Usage of the apparatus described above may be used in other medical treatments such as hemorrhoids, varicocela, and other vein diseases where blood vessels are congested and need to be ablated or eliminated.

Figure 4:
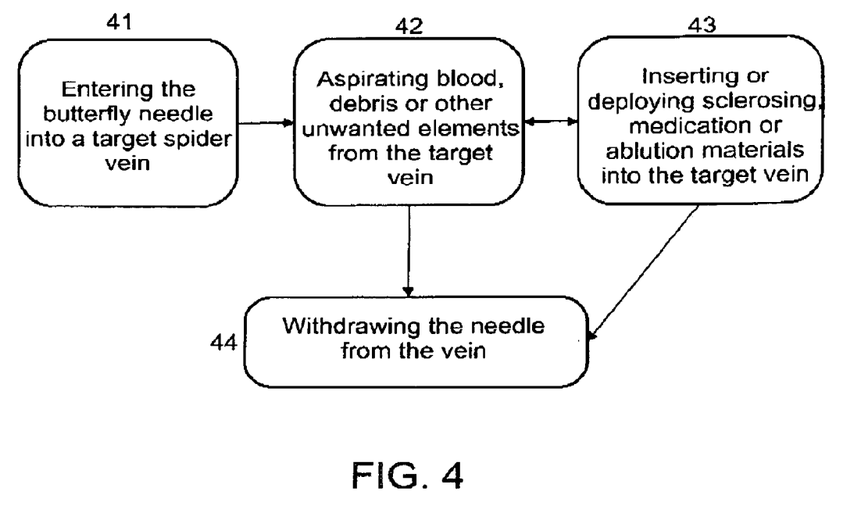
FIG. 4 is a schematic drawing showing a series of operations or processes that may be implemented to treat spider veins, according to some embodiments.

Reference is now made to FIG. 4, which is a schematic drawing showing a series of operations or processes that may be implemented to treat spider veins, according to some embodiments. As can be seen in FIG. 4, at step 41, the butterfly needle may be entered into a target spider vein. At step 42 a first reservoir control unit may be used to suck or aspirate blood from the target vein. At step 43 a second reservoir control unit may be used to insert or deploy sclerosing, medication or ablution materials into the target vein. The aspirating and/or deploying of materials may be controlled using a ratchet or other entering mechanism that may lock and selectively advance or retract the material deployment. Steps 42 and 43 may be executed consecutively, simultaneously, in reverse order or in any combination in accordance with the treatment required. At step 44 the needle may be withdrawn from the vein. Any combination of the above steps may be implemented. Further, other steps or series of steps may be used.

According to some embodiments, the aspirating and deployment steps may be implemented simultaneously, for example, using a dual control syringe that is adapted to implement the pushing of the one syringe puller in parallel with the pulling of the second syringe puller.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. An apparatus for eliminating spider veins, comprising:
   a dual syringe mechanism, said mechanism including a pusher for pushing sclerosant materials into a target vein via an outlet, and an extractor for extracting debris from said target vein via an inlet;
   a needle having two separate lumens for application into said target vein;
   a limited length connector which connects said pusher and said extractor such that said pushing causes pulling said extractor; and
   a Y-connector having first and second side arms respectively connecting said outlet and said inlet of said dual syringe mechanism to each said separate lumen of said needle;
   wherein said Y-connector includes first and second one way valves;
   wherein said first one way valve is disposed in said first arm and said one way second valve is disposed in said second side arm;
   wherein said dual syringe mechanism performs said pushing of sclerosant materials and said extracting of debris substantially simultaneously.

2. The apparatus of claim 1, wherein said dual syringe mechanism includes a locking mechanism configured to enable controlled advancing of the pusher.

3. The apparatus of claim 1, wherein said dual syringe mechanism includes a locking mechanism configured to enable controlled aspirating from said target vein by the syringe extractor.

4. The apparatus of claim 1, wherein one of the two separate lumens is an internal lumen, said Y-connector configured to provide passage between said internal lumen and the inlet.

5. A vein treatment device for ablating small veins, comprising:
   a small gauge needle for application into a target vein;
   a dual syringe mechanism having a first reservoir having an outlet for pushing sclerosant materials into a target vein, and having a second reservoir having an inlet for extracting debris from a target vein; and
   a Y-connector having first and second side arms respectively connecting said outlet and inlet of said dual syringe mechanism to said needle;
   wherein said Y-connector includes first and second one way- valves;
   wherein said first one way valve is disposed in said first side arm and said second one way valve is disposed in said second side arm;
   wherein said pushing of sclerosant materials and said extracting of debris are performed substantially simultaneously.

6. The treatment device of claim 5, comprising a syringe locking mechanism.

7. The treatment device of claim 6, wherein said syringe locking mechanism is adapted to provide stage by stage controlling of said pushing of sclerosant materials and said extracting of debris.

8. The treatment device of claim 7, wherein said stage by stage controlling is setup to provide increments of volumes ranging between 0.05 milliliters to 5 milliliters.

* * * * *